United States Patent [19]

Hanin

[11] Patent Number: 4,982,011

[45] Date of Patent: Jan. 1, 1991

[54] PRODUCTION OF ETHER/ETHER-ALCOHOL COMPOSITIONS

[75] Inventor: Jean A. A. Hanin, Rixensart, Belgium

[73] Assignee: Exxon Research and Engineering Co., Florham Park, N.J.

[21] Appl. No.: 386,952

[22] Filed: Jul. 31, 1989

Related U.S. Application Data

[63] Continuation of Ser. No. 283,749, Dec. 13, 1988, abandoned, which is a continuation of Ser. No. 31,588, Mar. 30, 1987, abandoned, which is a continuation of Ser. No. 803,093, Nov. 27, 1987, abandoned.

[30] Foreign Application Priority Data

Nov. 30, 1984 [GB] United Kingdom ............... 8430223
Nov. 30, 1984 [GB] United Kingdom ............... 8430224

[51] Int. Cl.$^5$ ............................................. C07C 41/05
[52] U.S. Cl. .................................. 568/678; 568/671; 568/591; 568/594; 252/364
[58] Field of Search ............... 568/678, 671, 591, 594; 252/364

[56] References Cited

U.S. PATENT DOCUMENTS

| | | |
|---|---|---|
| 2,595,096 | 4/1952 | Parker . |
| 2,671,119 | 3/1954 | Mertzweiller . |
| 2,757,203 | 7/1956 | Hale . |
| 2,779,794 | 1/1957 | Catherall . |
| 2,779,796 | 1/1957 | Munger . |
| 2,905,716 | 9/1959 | Buchner et al. . |
| 3,092,670 | 6/1963 | Gwynn et al. . |
| 4,048,233 | 9/1977 | Falbe et al. . |

FOREIGN PATENT DOCUMENTS 1411073 10/1975 United Kingdom .

*Primary Examiner*—Howard T. Mars
*Attorney, Agent, or Firm*—J. J. Mahon

[57] ABSTRACT

Ether/ether-alcohol rich compositions are produced by hydrogenating hydroformylation reaction products, separating an ether/ether-alcohol containing mixture from the hydrogenation product, and catalytically hydrogenating such mixture at 200°–250° C. and 30–100 atmospheres. The crude product is then reflux distilled to separate the ether/ether-alcohol rich compositions from lighter and heavier ends.

13 Claims, No Drawings

PRODUCTION OF ETHER/ETHER-ALCOHOL COMPOSITIONS

This is a continuation of application Ser. No. 283,749, filed Dec. 13, 1988 which is a continuation of Ser. No. 031,588 filed Mar. 30, 1987, which is a continuation of Ser. No. 803,093 filed Nov. 27, 1985 all now abandoned which is based on UK Nos. 84-30223 and 84-30224 filed Nov. 30, 1984.

This invention relates to certain ether/ether-alcohol compositions produced from the crude products of hydroformylation processes.

The hydroformylation process, in general terms, is a process involving the preparation of oxygenated organic compounds by the reaction of carbon monoxide and hydrogen (synthesis gas) with carbon compounds containing olefinic unsaturation. The reaction is performed under hydroformylation conditions in the presence of a carbonylation catalyst or catalyst precursor such as dicobaltoctacarbonyl, and results in the formation of a compound e.g. an aldehyde which has one more carbon atom in its molecular structure than the feedstock. Subsequent hydrogenation of the primary product leads to higher alcohols which may be used for example for conversion into plasticizers.

Typically in higher alcohol production the feedstock for a hydroformylation process is a commercial $C_6$–$C_{12}$ olefin fraction and the desired end product is the respective $C_7$–$C_{13}$ saturated alcohol or derived mixed alcohol product, produced by hydrogenation of the aldehyde oxonation product. By virtue of the nature of the feedstock commonly available to industry, and indeed of the catalyst and reaction parameters employed, the oxonation reaction inevitably yields a range of products due to the numerous secondary reactions which take place. The main commercial products of the hydroformylation reaction are aldehydes and alcohols, with side reactions in the oxonation, demetalling and hydrogenation sections of the process system usually producing some 5 to 20 wt. % of high boiling materials. Such high boiling materials, which represent a serious yield loss to the alcohol producer, are formed in large part by condensation, esterification and dehydration reactions.

In a conventional higher oxo alcohol process, the feedstock as described above is fed together with synthesis gas into an oxonation unit where catalytic hydroformylation takes place using e.g. hydrocobaltoctacarbonyl as the active catalyst species. The oxonation unit product passes to a unit for removing catalyst, and then to a hydrogenation unit where it is hydrogenated to form the desired higher alcohol. The product mixture at this stage, comprising the higher alcohol, the high boiling materials mentioned above and a low boiling fraction is then passed to a distillation unit where low boiling materials, high boiling materials and desired alcohol product are physically separated.

The low boiling material passing off overhead is a low value product, typically containing unreacted olefin feed and paraffins. The high boiling material usually contains dimers such as ethers and ether-alcohols (e.g. $C_{20}$ compounds in $C_{10}$ alcohol production) and trimers such as acetals (e.g. $C_{30}$ compounds in $C_{10}$ alcohol production) and heavier; although substantially alcohol free (apart from the heavy ether-alcohols), it may contain a minor amount of alcohol which has not been removed in the distillation stage where the higher alcohol major target product of the hydroformylation process is separated. Hitherto such high boiling materials or bottoms products have been conventionally purged from the system at low value. It is desirable, therefore, to develop a more profitable use of such materials, and after considerable assessment of the characteristics thereof a surprising new process has been proved.

Some uses have already been proposed for heavy oxo products, but principally these are directed to uses which involve further treatment of the high boiling materials in order to improve the economics of the oxo process. An example is the teaching of U.S. Pat. No. 4,048,233 (Ruhrchemie AG), according to which high boiling material (termed "thick oil" residue in that document) is converted to synthesis gas ($H_2$/CO mixture) by catalytic splitting at high temperatures using defined proportions of water vapour and carbon dioxide and a catalyst containing from 2 to 25 wt % nickel, optionally on a carrier such as alumina. The splitting takes place at temperatures of from 600° to 900° C. and pressures up to 30 atmospheres, and the synthesis gas product is recycled to the oxonation unit. Indeed the document teaches that after initial start up the synthesis gas product may constitute the sole supply of said gas to the system.

According to GB patent No. 1 411 073 (Kuhlmann) the aldehyde yield of an oxo process for producing aldehydes may be improved by a series of treatments which includes at one point hydrolysis of so-called heavy products. In the disclosed technique the crude product from the oxo reactor is first distilled to remove unreacted hydrocarbons, and then distilled to remove unreacted hydrocarbons, and then distilled to separate the desired aldehyde product. The remaining materials, products of secondary reactions in the oxo reactor, are, without any intermediate hydrogenation (which is considered undesirable and complicated according to page 1 lines 39–50 of the disclosure) then subjected to a further distillation to remove alcohols and formates. Following such removal the alcohol/formate distillate is dehydrogenated and returned to the hydroformylation outlet of the system. The residual heavy products are then catalystically steam hydrolysed at atmospheric pressure, 250°–400° C., and a preferred 1:1 w/w steam ratio to form a mixture of alcohols, aldehydes and residual heavy products, such mixture being recycled to the hydroformylation-output after removal of the residual heavy products.

It is noted here that the Kuhlmann method employs no hydrogenation stage; and furthermore that the nature of the secondary reaction products is considerably changed by incorporation of a hydrogenation step into the system. In particular the aldehyde content of the stream is minimised and of course, following hydrogenation there are no formates present in the stream, which formates are necessarily removed prior to hydrolysis in accordance with Kuhlmann.

U.S. Pat. No. 2,757,203 (Hale) also addresses the question of the secondary reactions occuring in the oxo process and in particular identifies that acetals may be formed, thus reducing the aldehyde/alcohol yield. Recognising that acetal formation is acid catalysed, Hale makes use of the equilibrium nature of the reaction by hydrolysing the acetal containing crude product, optionally after hydrogenation, in the presence of aqueous mineral acid at 212°–400° F. whilst simultaneously continuously distilling off the aldehyde. Hale provides no teaching to catalyse the hydrolysis with other than a mineral acid, nor does he propose performing the reaction on the heavy products obtained following removal of alcohol from the crude oxo product.

U.S. Pat. No. 2,779,794 (Catterall) teaches the heat soaking of the crude oxo product in contact with water in order to decompose cobalt catalyst compounds contained therein to an aqueous slurry, but the aim is simply catalyst removal, not any modification of the organic phase. Furthermore, there is no suggestion that catalytic steam hydrolysis might be used in the technique taught.

U.S. Pat. No. 2,905,716 (Buchner et al) teaches the removal of metal and acetals from a crude aldehyde containing oxo product by contacting the stream with water at 150°-200° C. in an elongate, unfilled reactor at elevated pressure, but makes no suggestion to use catalytic techniques nor any indication to recycle the resulting product.

U.S. Pat. No. 3,092,670 (Gwynn et al) teaches the removal of unreacted olefin from the crude oxo product by fractionating the demetalled product in the presence of steam. Subsequently the remaining material, containing polymeric secondary reaction products, is subjected to conventional hydrogenation to yield the desired alcohol product.

U.S. Pat. No. 2,779,796 (Munger) is also concerned with the removal of cobalt from crude oxo product streams and teaches the injection of live steam at 212°-400° F. into the crude product to achieve this objective. During such treatment all the heat required is supplied by the live steam and the crude product is not allowed to come into contact with any fixed heating surface having a temperature greater than the water/product mixture boiling point.

U.S. Pat. No. 2,595,096 (Parker) seeks to improve the alcohol yield of the oxo process by treating the bottoms obtained following oxonation, hydrogenation and removal of, first, unreacted hydrocarbons and then alcohols from the hydrogenated product stream. Such bottoms are said to contain polymerised aldehydes and ketones, high molecular weight ethers and secondary alcohols and polymerised hydrocarbons, principally acetals. The acetal content of the bottoms is hydrolysed with dilute mineral acid, with water (steam) or by other catalytic means to form quantities of alcohols and aldehydes which may themselves be recycled to the hydrogenation stage.

U.S. Pat. No. 2,671,119 (Mertzweiller) also seeks to obtain an improvement in the overall alcohol yield of the oxo process, by further treatment of the bottoms product obtained following distillation of alcohol from the product obtained by hydrogenation of the aldehydic product of the oxo reaction.

Such further treatment includes hydrogenation of the bottoms under conditions which are more severe than the primary hydrogenation conditions, to form a product comprising alcohols, esters, ethers and heavier unreacted material which is then passed to saponification to convert the ethers to alcohols (column 5 lines 69-73). The saponification stage may be omitted in certain circumstances (column 6 lines 29-32), however, it is clear that such saponification step is necessary if the process is to yield any increased amounts of valuable products (claim 7).

We are aware that certain hydroformylation-coproduct mixtures may be used as a viscosity regulator and/or low temperature performance improver for flexible polyvinyl chloride (PVC) compositions. A first such mixture comprises ether, ether alcohol and acetal components and is the bottoms product obtained by hydrogenation and subsequent distillation of the crude product derived from the catalytic hydroformylation of a $C_6$-$C_{12}$ olefinic feedstock with synthesis gas.

A second such mixture is the derivative obtained by subjecting such bottoms product to catalytic steam cracking at a temperature of from 260°-380° C. using as catalyst an active metal oxide or pseudo metal oxide.

It has now surprisingly been found that such mixtures are useful starting materials in a method for producing certain ether/ether alcohol rich compositions which have been shown to have useful properties.

According to the present invention there is provided a method of producing an ether/ether-alcohol rich composition useful in solvent or surfactant precursor applications which comprises (a) subjecting the product of an olefin hydroformylation reaction to hydrogenation; (b) distilling the hydrogenation product of (a) to separate a mixture comprising ether, ether-alcohol and acetal components from lighter ends; (c) catalytically hydrogenating said mixture of step (b) at a temperature of 200°-250° C. and a pressure of 30-100 atmospheres to form an alcohol enriched product mixture; and (d) subjecting the product mixture of step (c) to reflux distillation to separate (i) the desired ether/ether-alcohol rich composition containing at least 90 wt % of ether/ether-alcohol from (ii) a lighter alcohol rich fraction and (iii) a heavier acetal rich fraction. The hydroformylation reaction conditions may be considered as entirely conventional and in accordance with the general hydroformylation process disclosures made hereinbefore. Thus the catalyst may be for example cobalt based and the operating temperatures, pressures and other conditions such as synthesis gas composition may be controlled in accordance with the usual expertise of the person skilled in the art to maximise yield of the desired higher alcohol product. For example the hydroformylation reaction may be carried out at a pressure of 150-300 atm, and a temperature of from 120°-190° C.

The catalyst may be used in desired active form, for example in a concentration of from 0.05-3 wt % as metal based on the olefinic feed. Typically the synthesis gas used might have a $H_2$:CO volume ratio in the range 0.9:1-1.5:1. The catalyst is generally separated from the product mixture prior to hydrogenation step (a) of the invention.

The catalytic hydrogenation step (c) of the method is preferably carried out at a temperature in the range 220°-240° C. The preferred pressure of operation is in the 45-65 atm range. It has been found that the hydrogenation reaction to the desired alcohol enriched product mixture proceeds satisfactorily at a space velocity of from 0.2-2 vol/vol/hour, with the more preferred space velocity range being from 0.75-1.25 vol/vol/hour. By space velocity is meant the hourly flow by volume of the liquid reactants per unit volume of catalyst employed. Any suitable hydrogenation catalyst may be employed, but the so-called copper chrome (also termed Cu/Cr or copper-chromium oxide or copper-chromite) catalyst is preferred. Another preferred catalyst comprises supported nickel.

In a preferred embodiment, the ether/ether-alcohol rich composition (i) is itself separated during the reflex distillation into (ia) an ether-rich fraction containing at least 80% wt ether and (1b) an ether-alcohol rich fraction containing at least 90 wt % ether-alcohol.

The mixtures which have been found useful as the feed to step (c) are preferably those derived from hydroformylation reactions using olefinic feedstocks having carbon numbers of 8 or 9.

The ether-alcohol fraction (ib) as mentioned above and produced in accordance with the method of the invention has, with a substantially C9 olefinic feedstock, been identified as having the molecular formula $$C_9H_{19}-CH_2-O-CH(CH_2OH)-C_9H_{19}$$

and isomeric forms thereof such as $$C_9H_{19}-CH_2-O-CH_2-CH(CH_2OH)-C_8H_{17}$$

The terminal alkyl groups of such molecules are derived from numerous side reactions in the various process steps which are necessary, and so are not necessarily symmetrical groups.

Similarly, in the case where the feedstock to the hydroformylation reaction is substantially C8 olefin the ether-alcohol fraction (ib) will have the molecular formula identified as $$C_8H_{17}-CH_2-O-CH(CH_2OH)-C_8H_{17}$$

and isomeric forms thereof such as $$C_8H_{17}-CH_2-O-CH_2-CH(CH_2OH)-C_7H_{15}$$

Again, the terminal alkyl groups will not necessarily be symmetrical.

To yield end product compositions (i) having desired and useful properties it is preferred to conduct step (b) in a manner such that the ether, ether-alcohol and acetal containing product thereof has at least one, and preferably many or even all of the following characteristics: specific gravity of from 0.81–0.87, more preferably 0.83–0.85; and/or distillation characteristics at atmospheric pressure of initial boiling point (IBP) from 240°–310° C., more preferably 260°–300° C. and final boiling point (FBP) from 310°–380° C., more preferably 330°–350° C.; and/or a flash point of from 140°–170° C.; and/or an acidity (mg KOH/g) of from 0.1–0.4; and/or a hydroxyl number (mg KOH/g) of from 80–130; and/or a carbonyl number (mg KOH/g) of from 3–6; and/or a pour point of less than −30° C.; and/or a saponification number (mg KOH/g) of from 5–10.

It has been found that conducting step (b) to produce mixtures comprising from 15–25 wt % ether component, from 45–65 wt % ether alcohol component from 5–25 wt % acetal component and from 2–10 wt % of ester component results in a final product of the method which has particularly useful and desirable properties. Depending on the distillation conditions applied in step (b) the bottoms product may contain a minor amount, for example up to 5 wt %, of light alcohol components. However it is preferred that such alcohols be substantially completely removed in order to increase the carbon number range lower limit for alcohols in the mixture.

Preferably the mixtures used comprise a major proportion of compounds with carbon numbers in the dimer range (based on the starting olefin and target oxo-product) and they may also contain a small amount e.g. up to 2 wt % of extremely heavy compounds.

In accordance with a particularly preferred embodiment of the invention, it is preferred that step (c) is conducted such that the product mixture of step (c) has at least one, preferably many and most preferably all of the following characteristics: a specific gravity of from 0.81–0.87; distillation characteristics at atmospheric pressure of initial boiling point from 240°–310° C. and final boiling point 310°–380° C.; a flash point of from 140°–170° C.; an acidity (mg KOH/g) of from 0.05–0.1; a hydroxyl number (mg KOH/g) of from 120–140; a saponification number (mg KOH/g) of from 2–4; a carbonyl number (mg KOH/g) of from 0.5–2.0; and a pour point of less than −30° C.

In general, step (c) may be conducted on the defined feed streams under hydrogenation conditions which are no more severe than those employed for the hydrogenation stage (a) of the hydroformylation alcohol production process proper.

Step (d) of the method of the invention requires the hydrogenated product of step (c) to be subjected to reflux distillation i.e. fractionation in order to yield a lighter alcohol rich fraction (ii) and a heavier acetal rich fraction (iii) in addition to the ether/ether-alcohol rich composition (i) which is the target product of the method. Although the individual components of composition (i) may be known or may be present in the by-products of hydroformylation processes, the value of the method of the invention is that it permits the operator to recover from his process streams a composition which is rich in heavy oxygenated by-products which have been shown to have properties which make such compositions valuable not only as industrially useful solvent or diluent systems, but also as starting materials in the production of long chain oxygenated materials such as detergents and surfactants. The particular distillation conditions applied in step (d) control the particular nature of composition (i) in terms of its composition, whereas step (c) has a great effect on many of its characteristic parameters.

Adjustment of the properties of the final product is thus possible and within the abilities of the person of skill in the art, by appropriate control over the conditions of steps (c) and (d). In a preferred embodiment, step (d) is performed such that the alcohol rich fraction (ii) is one which contains at least 75 wt % alcohol, with the balance comprising chiefly ethers.

The acetal rich fraction (iii) is preferably that which comes off last or remains as bottoms in the reflux distillation stage, and comprises at least 70 wt % acetal with the remainder being chiefly ether-alcohols. The intermediate fraction constitutes the composition (i) which comprises at least 90 wt % ether/ether-alcohol. It is particularly preferred that such composition (i) be separated during the reflux distillation into an ether rich fraction (ia) which contains at least 80 wt % ether, with the remainder being chiefly ether alcohol; and an ether alcohol rich fraction (ib) which contains at least 90 wt % ether alcohol, with the remainder being chiefly ether. These individual components (ia) and (ib) of composition (i) have themselves been shown to have useful properties and so also is the method of producing them industrially useful.

With regard to separation of the product of step (c) into the desired fraction according to step (d), it will be appreciated that separation by temperature ranges is most convenient to the operator. Preferably step (d) is performed using a reflux distillation column with the appropriate number of plates, and for convenience the distillation is performed at reduced pressure. Thus the temperature range for each fraction of step (d) will depend on the applied pressure. However on conversion of these temperatures to atmospheric pressure, it has been found that in a preferred embodiment of the method whereby the target alcohol of the hydroformylation reaction is a C10 alcohol, i.e. using a C9 olefin feed, fraction (ii) is preferably that which distils off at 170°–305° C. (converted to atmospheric pressure distillation); fraction (i) is that distilling at 305°–370° C.; and fraction (iii) is that which distils off above 370° C. under atmospheric pressure. In the particularly preferred embodiment where composition (i) is itself split, the two fractions are preferably those distilling at 305°–340° C. for the ether rich fraction (ia) and 340°–370° C. for the ether-alcohol rich fraction (ib).

In one particular embodiment of the method where C10 alcohol is the target alcohol of the hydroformylation reaction, the conditions are preferably adjusted so that the viscosity of the product of step (c) is from 45–55 centistokes. Fractionation is then carried out to yield compositions (ia) having a low viscosity of 12–18 centistokes, (ib) with viscosisty 100–220 centistokes and (iii) with viscosity 150–200 centistokes, all at room temperature. These viscosity ranges make the products of the method particularly well suited for certain applications such as diluent and solvent systems.

The distillation temperature ranges for step (d) will be different for different target alcohols of the hydroformylation. For example when the products being hydrogenated in accordance with step (c) are heavy mixtures formed in C9 alcohol production from C8 olefins, it is preferred that composition (ib) is that which fractionates at 315°–345° C. (converted to atmospheric pressure).

It is particularly preferred that the method step conditions are controlled such that the ether rich fraction (ia) separated in step (d) is one having one or more, preferably all, of the following characteristics: carbonyl number (mgKOH/g) 0.5–2; acid number (mgKOH/g) less than 0.3, more preferably less than 0.1; saponification number (mgKOH/g) 2–7, more preferably 3–5; and hydroxyl number (mgKOH/g) less than 50.

The ether-alcohol rich fraction (ib) separated in step (d) is preferably the one having one or more, preferably all, of the following characteristics (measured in mgKOH/g): carbonyl number 0.5–2; acid number less than 0.1; saponification number 1–5, more preferably 2–5; and hydroxyl number 160–190, more preferably 165–175.

As mentioned hereinbefore, an alternative mixture used for producing the ether/ether-alcohol rich compositions is a derivative of the mixture formed in step (b). Thus in accordance with a preferred modification of the method of the invention, the method is one wherein step (b) includes a method according claim 1 wherein step (b) includes the additional stage (b') of subjecting said mixture comprising ether, ether-alcohol and acetal components to catalytic steam cracking at a temperature of from 260°–380° C. using as catalyst an active metal oxide or pseudo-metal oxide to form an ether enriched heavy product mixture and lighter materials and wherein step (c) is performed on said heavy product mixture. This modification may be viewed as a further and beneficial use of the so-called HOF residue which is formed in a process already known to the applicants which process is primarily concerned with the production of higher alcohols from an olefinic feedstock. Such process comprises hydroformylating the feedstock with synthesis gas in the presence of a hydroformylation catalyst to form a product mixture containing higher aldehyde, alcohol, unreacted feed and secondary products; removing catalyst therefrom; hydrogenating the substantially catalyst free mixture to convert the higher aldehyde to higher alcohol; distilling the higher alcohol-containing product mixture to separate (i) a lower boiling Light Oxo Fraction (LOF) and (ii) the desired higher alcohol from (iii) a higher boiling Heavy Oxo Fraction (HOF); subjecting the HOF to catalytic steam cracking at a temperature of from 260° to 380° C. using as catalyst an active metal oxide or pseudo-metal oxide, to form HOF residue and a cracked HOF mixture comprising a major proportion of higher alcohol and higher aldehyde, and a minor proportion of olefin and saturated hydrocarbon; and recycling the cracked HOF mixture to the hydroformylation or hydrogenation stage of the process.

The catalysts which may be employed in step (b) are those which promote hydrolysis of the components of the ether, ether-alcohol and acetal containing product of step (b). Thus the catalyst is selected such that the hydrolysis reaction takes place at the rather severe conditions defined to yield a mixture which contains higher alcohols and aldehydes, together with the ether-enriched heavy product mixture which is then passed on for treatment in accordance with step (c) of the present method. The catalysed reactions performed under the specified steam cracking conditions may be for example acetal hydrolysis, ester hydrolysis, or ether hydrolysis.

It has been found that the desired reactions take place in the presence of metal or pseudo-metal oxides in the active state, such as silica, alumina or titanium dioxide, or mixed silica/alumina. It is particularly preferred to employ alumina as the hydrolysis catalyst. Such catalysts, under the temperature specified, at least partially convert the products of distillation step (b) to alcohols and aldehydes, with the balance being the desired heavy oxygenated products.

The temperature at which the steam cracking step is performed is most preferably in the relatively high range of 290° to 360° C., and preferably at pressures of from 100 to 1000 kPa (1–10 bar), more preferably 1–3 atm abs. It is preferred that the hydrolysis of the HOF is performed with the weight ratio of steam and HOF in the range 0.1:1 to 2:1, more preferably 0.2:1 to 1.2:1. For economic reasons the optimum range has been found to be from 0.15:1 to 0.5:1.

The ether/ether-alcohol rich composition (i) produced by application of the modified method as described hereinbefore preferably comprises at least 80 wt % ether, with the balance being substantially ether-alcohols. It has been found that in the case where the principal feed to the hydroformylation reaction is C9 olefin, the major ether component of the desired composition (i) has the molecular formula $C_{10}H_{21}$—O—$C_{10}H_{21}$, with the alkyl groups attached through the oxygen atom not necessarily being symmetrical. In the case where C8 olefin is the principal feed, then the desired composition (i) has been identified as largely comprising compounds having the molecular structure $C_9H_{19}$—OC—$_9H_{19}$; again, the terminal alkyl groups are not necessarily symmetrical since they are derived from a complex reaction pathway.

The steam cracking in accordance with the modified invention yields a HOF residue which is typically oxygenated dimers and trimers ($C_{20}$–$C_{30+}$ materials for a $C_{10}$ alcohol), with preferably less than 10 wt % of monomeric components.

Preferably the heavy product mixture formed in step (b') comprises from 45-75 wt % ether component, from 20-35 wt % ether-alcohol component, from 1-6 wt % acetal component, from 0-10 wt % alcohol/aldehyde component and from 0-7 wt % ester component, whilst the preferred product mixture of step (c) produced therefrom has the same components in the same proportional ranges, save that the ether-alcohol component may be present in smaller amounts, say from 10-35 wt %, and the alcohol/aldehyde components in larger amounts, say up to 15 wt. %.

Whether or not present in the above amounts the heavy product mixture formed in step (b'), and the product mixture of step (c), preferably have one or more of the following characteristics: specific gravity of from 0.81-0.87; initial boiling point (atmospheric pressure) of 240°-310° C.; final boiling point (atmospheric pressure) of 310°-380° C.; flashpoint of 140°-170° C. and a pour point of less than −30° C. Preferably, too, the step (b') heavy product has one or more of a carbonyl number (mg KOH/g) of from 20-30; acidity (mq KOH/g) of from 2-7; saponification number (mg KOH/g) of from 10-20 and/or hydroxyl number (mg KOH/g) of from 30-50. Correspondingly the product of step (c) preferably has one or more of the values 0.5-3.0; 0.5-2.0; 5-10; and 70-90 respectively.

In the modified method of the invention; the reflux distillation step (d) is preferably performed such that the fraction corresponding to composition (i) is removed at temperatures in the range 310°-370° C. (adjusted to atmospheric pressure) for the case where the target alcohol of the hydroformylation reaction is a decanol. The alcohol rich fraction (ii) is preferably the one which distils at 170°-310° C. (one atmosphere) and contains at least 75 wt % alcohol with the balance being mainly ether components; the remaining bottoms fraction is the one boiling at temperatures above 370° C. and contains at least 80 wt % acetal with the balance being mainly ether alcohols and heavier components. In the case where the target alcohol is C9, the composition (i) is preferably the one which distils at 285°-345° C. (adjusted to atmospheric pressure).

With regard to the chemical characteristics of the desired product, the ether rich composition (i) produced by the modified method incorporating the additional step (b') is preferably the fraction having one or more, preferably all, of the following characteristics (measured in mg KOH/g): carbonyl number 0.5-2.5, more preferably 1-2.5; acid number less than 1.0, more preferably less than 0.25; saponification number from 4-10, more preferably 5-10; and hydroxyl number less than 50.

The invention is illustrated by the following examples of which Examples 1 and 3 demonstrate a method of producing useful ether and ether-alcohol rich compositions from the heavy oxo fraction of a hydroformylation reaction product mixture; and Examples 2 and 4 demonstrate the production of useful ether rich compositions from the heavy oxo fractions of a hydroformylation product which fractions have been subjected to a steam cracking operation.

EXAMPLE 1

A hydroformylation process for producing higher alcohol was performed using a feed comprising (i) syn gas containing hydrogen and carbon monoxide in a molar ratio of 1.16:1 and (ii) a commercially available stream of branched nonenes including also about 2 wt % octenes and about 8 wt % decenes. The olefin feed was delivered at a rate of 1.5 l/hr (1115 g/hr), and the syn gas at a rate of 640 standard l/hr, into three 1.0 liter capacity oxonation reactors arranged in series, and the reaction was carried out at a pressure of 300 atm and a temperature of 175° C., using a cobalt catalyst at 0.3 wt % based on the feed. The resultant crude oxo product containing higher aldehyde was decobalted to less than 10 ppm cobalt in conventional manner by neutralizing the cobalt hydrocarbonyl with sodium hydroxide and washing with water, and thereafter was fed to a conventional hydrogenation train where, using Cu/Cr and Ni catalysts, a hydrogen pressure of 50 bar and a temperature of 120°-170° C. a product mixture containing the desired higher alcohol was formed. This product mixture was then distilled under vacuum in accordance with step (b) of the method of the invention to produce three fractions, a light oxo fraction (LOF), a higher alcohol fraction (HA) and a bottoms product or heavy oxo fraction (HOF) as shown in Table 1.

TABLE 1

| Fraction | Amount | Alcohol content | Boiling Range |
|---|---|---|---|
| LOF | 150 g/hr | ≦0.5 wt % | 125-187° C. |
| HA | 1010 g/hr | | 187-217° C. |
| HOF | 223 g/hr | ≦3 wt % | >217° C. |

The higher alcohol yield (chiefly $C_{10}$, with minor amounts of $C_9$ and $C_{11}$) was 90.58 g per 100 g of feed olefin.

By analysis the HOF, that is the bottoms product or step (b) product mixture, was shown to comprise approximately:

| 2 wt % | $C_9$-$C_{11}$ alcohols |
|---|---|
| 85 wt % | $C_{18}$-$C_{22}$ ethers, ether-alcohols and esters |
| 12 wt % | $C_{27}$-$C_{33}$ acetals |
| 1 wt % | Heavies |

This material was characterised by:

| Carbonyl number (mg KOH/g) | 3.12 |
|---|---|
| Acid number (mg KOH/g) | 0.19 |
| Saponification number (mg KOH/g) | 7.10 |
| Hydroxyl number (mg KOH/g) | 123.2 |

Step (c) of the method was performed on the HOF by passing the crude ether, ether-alcohol and acetal containing material through a hydrogenation reactor at a space velocity of 0.5 vol/vol/hour. The pressure employed was 56 bars and the hydrogenation was carried out over a copper-chromite catalyst (Girdler G 22RS) at 230° C. The alcohol enriched product mixture was found to have the following composition and characteristics:

| 7 wt % | $C_9$-$C_{11}$ alcohols | |
|---|---|---|
| 84 wt % | $C_{18}$-$C_{22}$ ethers, ether-alcohols, esters | |
| 9 wt % | $C_{27}$-$C_{33}$ acetals (including a small amount of heaviers) | |
| Carbonyl number (mg KOH/g) | | 0.9 |
| Acid number (mg KOH/g) | | 0.1 |
| Saponification number (mg KOH/g) | | 3.4 |
| Hydroxyl number (mg KOH/g) | | 134 |

The proportion of ether, ether alcohol and esters in the above composition may be deduced from the compositional breakdown as provided in Table 2.

Step (d) of the method was performed by subjecting the above-defined hydrogenation product mixture to a vacuum reflux distillation at a pressure of 5-15 millibars and a reflux ratio of 2, with removal of four fractions from the distillation column. The first fraction was the alcohol rich material designated (ii) hereinbefore, and the bottoms fraction was the heavy acetal rich fraction designated (iii) hereinbefore. The second and third fractions to come off from distillation together comprised the ether/ether alcohol rich composition designated (i) hereinbefore, although simultaneously in the reflux distillation the composition (i) was split into its ether and ether-alcohol rich fractions designated herein (ia) and (ib) respectively. The ether-alcohol fraction (ib) was subjected to structural analysis and found to comprise for the most part a $C_{21}H_{44}O_2$ ether alcohol having a molecular structure which is an isomeric equilibrium of about 90% (I) $C_9H_{19}CH_2-O-CH(CH_2OH)-C_9H_{19}$ and about
10%(II)
$C_9H_{19}-CH_2-O-CH_2-CH(CH_2OH)-C_8H_{17}$ The exact structure of the terminal alkyl groups was not determined, but could in fact be any combination of groups desirable from the feedstock and reaction by-products. The balance of fraction (ib) was equivalent products derived from the small proportion of $C_8$ and $C_{10}$ olefin in the feedstock.

The distillation and other characteristics of the materials produced in step (d) of the method are shown in Table 2.

TABLE 2

|  | Alcohol (ii) | Ether (ia) | Ether-Alcohol (ib) | Bottoms (iii) |
|---|---|---|---|---|
| Boiling range °C. (atmospheric pressure) | 175-312 | 312-340 | 340-360 | >360 |
| wt % distilled | 9 | 23 | 53 | 15 |
| Composition wt % |  |  |  |  |
| $C_9$-$C_{11}$ alcohols | 78 |  |  |  |
| $C_{18}$-$C_{20}$ ether |  | 94 |  |  |
| $C_{19}$-$C_{21}$ ether/alcohol |  |  | 97 |  |
| Acetals and heaviers |  |  |  | 60 |
| Characteristics |  |  |  |  |
| Carbonyl number | 3.3 | 1.6 | 1.3 | 2.1 |
| Acid number | 0.4 | 0.04 | 0 | 0.16 |
| Saponification number | 3.4 | 3.04 | 3.0 | 0.37 |
| Hydroxyl number | 235 | 37 | 174 | 15.2 |
| Specific gravity @ 20° C. | 0.8355 | 0.8305 | 0.8679 | 0.8727 |
| Flash point (°C.) | 103 | 166 | 200 | 226 |
| Pour point (°C.) |  | <-40 | <-40 |  |
| Viscosity (cs) 15° C. | 22.11 | 14.01 | 104.73 | 156.93 |
| 20° C. | 17.45 | 11.43 | 74.08 | 110.69 |
| 30° C. | 11.39 | 8.02 | 40.03 | 59.85 |
| 40° C. | 7.89 | 5.94 | 23.99 | 35.23 |

EXAMPLE 2

The bottoms product mixture (HOF) produced in Example 1 was subjected to additional step (b') by passage in upflow manner and in admixture with half its weight of steam into a steam cracking reactor. The reactor was packed with an active alumina catalyst ALCOA H151 and operated at 318° C., and a pressure of 1.2 atm. The flow of HOF/steam through the reactor was such as to correspond to a space velocity of 0.5 v/v/hr expressed as volume of HOF per volume of catalyst per hour. After cracking, the cracked product was subjected to flashing at 200° C., to produce an overhead stream comprising a so-called cracked HOF mixture and water (steam), and a bottoms stream of an ether-rich heavy product mixture (also termed HOF residue). The HOF residue comprise a major proportion of oxygenated compounds of carbon number $C_{18}$-$C_{30}$ (predominantly $C_{18}$-$C_{22}$) with some even heavier products, and a minor proportion of alcohol/aldehyde/olefin components. The cracked HOF mixture obtained after condensation of the overheads and separation of water comprised a small proportion of HOF residue, a smaller proportion of an olefin fraction, generally $C_8$-$C_{11}$ olefins with predominantly $C_{10}$ olefin and a very low level of saturated hydrocarbon, and a major proportion of an alcohol/aldehyde mixed fraction with carbon numbers $C_9$-$C_{11}$, predominantly $C_{10}$.

By analysis the HOF residue was shown to have the following composition and characteristics:

| 8 wt % | $C_9$-$C_{11}$ alcohol/aldehydes |  |
|---|---|---|
| 82 wt % | $C_{18}$-$C_{22}$ ethers, ether alcohols, esters |  |
| 10 wt % | acetals and heaviers |  |
| Carbonyl number (mg KOH/g) |  | 26.8 |
| Acid (mg KOH/g) |  | 4.6 |
| Saponification (mg KOH/g) |  | 16.2 |
| Hydroxyl (mg KOH/g) |  | 40.3 |

Step (c) of the method was performed by passing the product of modification step (b') through a hydrogenation reactor at a space velocity of 0.45 vol/vol/hour, under a pressure of 54 bars and at temperature 233° C. The catalyst was Girdler G 22RS copper-chromite. The product mixture of step (c) was found to have the following composition and characteristics:

| 13 wt % | $C_9$-$C_{11}$ alcohols |  |
|---|---|---|
| 79 wt % | $C_{18}$-$C_{22}$ ethers, ether alcohols, esters |  |
| 8 wt % | Acetals and heaviers |  |
| Carbonyl number (mg KOH/g) |  | 0.8 |
| Acid (mg KOH/g) |  | 0 5 |
| Saponification (mg KOH/g) |  | 7.9 |
| Hydroxyl (mg KOH/g) |  | 82.2 |

The proportions of ether, ether alcohol and ester in the above composition may be deduced from the products as listed in Table 3.

Step (d) of the modified method was performed by subjecting the step (c) product to vacuum distillation at 10-15 mbar with a reflux ratio of 2. The composition and characteristics of the fractions separated are set out in Table 3, in which alcohol (ii) was the first fraction removed, and ether rich composition (i) was the second fraction, with the bottoms being the fraction designated (iii) hereinbefore. In this case, composition (i) was not simultaneously separated into its components. Analysis of composition (i) showed that it comprised for the most part an ether corresponding to the formula:

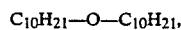
$C_{10}H_{21}-O-C_{10}H_{21}$, analysis was not performed to establish the precise nature of the terminal alkyl groups, but these would derive from the feed olefin and by products in the method. The balance of composition (i) was the corresponding ether-alcohol, and the associated ethers/ether alcohols deriving from the minor components of the original feedstock olefin.

TABLE 3

| | Alcohol (ii) | Composition (i) | Bottoms (iii) |
|---|---|---|---|
| Boiling range °C. (atmospheric pressure) | 170-310 | 310-370 | >370 |
| wt % distilled | 17 | 71 | 12 |
| Composition wt % | | | |
| $C_9-C_{11}$ alcohols | 76 | | |
| $C_{18}-C_{20}$ ether | | 85 | |
| $C_{19}-C_{21}$ ether/alcohol | | 13 | |
| Acetals and heaviers | | | 66 |
| Characteristics | | | |
| Carbonyl number | 1.4 | 1.9 | 0.2 |
| Acid number | 0.8 | 0.2 | 1.33 |
| Saponification number | 1.5 | 9.6 | 12.8 |
| Hydroxyl number | 172 | 37.0 | 29.8 |
| Specific gravity @ 20° C. | | 0.83 | 0.8625 |
| Flash point (°C.) | | 164 | |
| Pour point (°C.) | | <-40 | |
| Viscosity (cs) 15° C. | | 17.99 | |
| 20° C. | | 14.23 | |
| 30° C. | | 9.84 | |
| 40° C. | | 7.18 | |

EXAMPLE 3

A hydroformylation process was performed in the same apparatus as Example 1 under conditions of 165° C., 300 atm and using cobalt catalyst at 0.15 wt % based on the feed. However, the feed in this case was 1.5 l/hr (1095 g/hr) of a commercial branched octene feed containing in addition to $C_8$ olefin, about 1% of $C_7$ olefins and about 10% of $C_9$ olefins. The syn gas was employed at a rate of 750 standard liters/hr, and contained hydrogen and carbon monoxide in a ratio of 1.18:1.

Demetalling and hydrogenation of the crude product was performed as in Example 1, with the hydrogenated product being separated by distillation in accordance with step (b) of the method into the three fractions as shown in Table 4. The hydroformylation bottoms product mixture (HOF) was the fraction boiling at 206° C. and above.

TABLE 4

| Fraction | Amount | Alcohol content | Boiling Ranges |
|---|---|---|---|
| LOF | 150 g/hr | ≦0.5 wt % | 113-184° C. |
| HA | 1013 g/hr | | 184-206° C. |
| HOF | 219 g/hr | ≦3 wt % | >206° C. |

This yield of higher alcohol corresponds to an amount of 92.5 g per 100 g of feed olefin.

By analysis the HOF was shown to have the composition:

| 1 wt % | $C_8-C_{10}$ alcohols | |
|---|---|---|
| 87 wt % | $C_{16}-C_{20}$ ethers, esters and ether-alcohols | |
| 11 wt % | $C_{24}-C_{30}$ acetals | |
| 1 wt % | Heavies | |
| The HOF was characterized by | | |
| Carbonyl number (mg KOH/g) | | 4.9 |
| Acid number (mg KOH/g) | | 0.15 |
| Saponification (mg KOH/g) | | 8.2 |
| Hydroxyl (mg KOH/g) | | 128.0 |

Step (c) of the method was performed by passing the crude ether, ether alcohol and acetal containing material through a hydrogenation reactor at a space velocity of 0.58 vol/vol/hour, pressure of 56 bars and temperature of 240° C. The catalyst employed was Girdler G22RS copper-chromite. The alcohol enriched product mixture was found to have the following composition and characteristics:

| 8 wt % | $C_8-C_9$ alcohols | |
|---|---|---|
| 83 wt % | $C_{16}-C_{20}$ ethers, ether alcohols, esters | |
| 9 wt % | acetals (including a small amount of heaviers) | |
| Carbonyl number (mg KOH/g) | | 1.5 |
| Acid number (mg KOH/g) | | 0.05 |
| Saponification (mg KOH/g) | | 4.9 |
| Hydroxyl (mg KOH/g) | | 130.0 |

The proportion of ether, ether-alcohol and esters in the above compositions may be deduced from the product breakdown as provided in Table 5.

Step (d) was performed by subjecting the above mixture to vacuum reflux distillation at 10-15 mbar and a reflux ratio of 2. As with Example 1, the first fraction was alcohol (ii) and the final bottom was the heavy acetal fraction (iii). The intermediate composition (i) was simultaneously separated into ether fraction (ia) and ether-alcohol fraction (ib). A structural analysis of fraction (ib) showed it to be principally a $C_{19}H_{40}O_2$ ether primary alcohol having a molecular structure corresponding to an isomeric equilibrium of about 90% (III) $C_8H_{17}-CH_2-O-CH(CH_2OH)-C_8H_{17}$
and about 10%
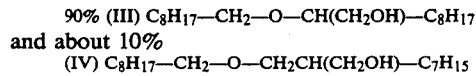
(IV) $C_8H_{17}-CH_2-O-CH_2CH(CH_2OH)-C_7H_{15}$ The exact structure of the terminal alkyl groups was not determined.

The distillation and other characteristics of the fractions produced in step (d) are shown in Table 5.

TABLE 5

| | Alcohol (i) | Ether (ia) | Ether-Alcohol (ib) | Bottoms (iii) |
|---|---|---|---|---|
| Boiling range °C. (atmospheric pressure) | 150-290 | 290-320 | 320-345 | >345 |
| wt % distilled | 10 | 20 | 56 | 14 |
| Composition wt % | | | | |
| $C_8-C_{10}$ alcohols | 80 | | | |
| $C_{16}-C_{20}$ ether | | 90 | | |
| $C_{17}-C_{19}$ ether-alcohol | | | 98 | |
| Acetals and heaviers | | | | 64 |
| Characteristics | | | | |
| Carbonyl number (mg KOH/g) | 2.2 | 1.7 | 1.2 | |
| Acid number | 0.5 | 0.2 | 0 | |
| Saponification number | 1.5 | 4.3 | 1.0 | |
| Hydroxyl number | 188 | 29 | 165 | |
| Specific gravity @ 20° C. | 0.8316 | 0.8281 | 0.8663 | 0.8713 |
| Flash point (°C.) | | 140 | 170 | |
| Pour point (°C.) | | <-40 | <-40 | |
| Viscosity (cs) 15° C. | | 11.87 | 82.47 | |
| 20° C. | | 9.79 | 59.62 | |
| 30° C. | | 6.99 | 33.35 | |
| 40° C. | | 5.22 | 20.21 | |

EXAMPLE 4

The bottoms product (HOF) mixture produced in Example 3 was subjected to additional step (b') by catalytic steam cracking in a reactor packed with ALCOA H 151, at 310° C., a pressure fo 1.1 atm and a space velocity of HOF equal to 0.47 v/v/hr. The amount of steam used was 25% of the weight of HOF. Two cracked product streams were obtained following flash at 196° C. and removal of water. The ether-rich mixture (HOF residue) stream was the flash liquid phase and was found to comprise $C_{10}$-$C_{27}$ oxygenated compounds, predominantly $C_{16}$-$C_{20}$ materials, with 7 wt % other minor components including some aldehyde, alcohol and olefin. The other stream being the flash vapour phase, comprised an olefin fraction (10 wt %) which was a mixture of $C_7$-$C_{10}$ olefins, predominantly $C_9$'s together with small amounts of saturated hydrocarbons, and an alcohol/aldehyde fraction (69.2 wt %) containing a $C_8$-$C_{10}$ carbon number range, with a major amount of $C_9$ alcohols/aldehydes.

By analysis the HOF residue was shown to have the following composition and characteristics:

| | |
|---|---|
| 7 wt % | $C_8$-$C_{10}$ alcohols/aldehydes |
| 83 wt % | $C_{16}$-$C_{20}$ ethers, ether-alcohols, ester |
| 10 wt % | acetals and heaviers |
| Carbonyl number (mg KOH/g) | 26.0 |
| Acid number (mg KOH/g) | 2.5 |
| Saponification (mg KOH/g) | 18.0 |
| Hydroxyl (mg KOH/g) | 23.0 |

Step (c) was performed by passing the product of step (b') through a hydrogenation reactor at space velocity 0.58 vol/vol/hour employing pressure conditions of 54 bars and a temperature of 235° C. The catalyst was Girdler G 22 RS copper-chromite. The product had the following composition and characteristics.

| | |
|---|---|
| 11 wt % | $C_8$-$C_{10}$ alcohols |
| 77 wt % | $C_{16}$-$C_{20}$ ethers, ether alcohols, esters |
| 12 wt % | acetals and heaviers |
| Carbonyl number (mg KOH/g) | 2.0 |
| Acid number (mg KOH/g) | 1.0 |
| Saponification (mg KOH/g) | 14.0 |
| Hydroxyl (mg KOH/g) | 47 |

The proportions of ether, ether alcohol and esters in the above compositions may be deduced from the breakdown provided in Table 6.

Step (d) was performed on the product of step (c) by vacuum reflux distillation at 10–15 mbar and a reflux ratio of 2. The compositions and characteristics of the fractions separated are set out in Table 6, in which alcohol (ii) was the first fraction separated, ether rich composition (i) was the second fraction and the bottoms was the fraction designated (iii). Analysis of composition (i) showed it to be for the most part an ether of formula $C_9H_{19}$—O—$C_9H_{19}$. The balance of composition (i) was the corresponding ether alcohol, and components derived from the minor amounts of other than $C_8$ olefins in the original feedstock.

TABLE 6

| | Alcohol (ii) | Composition (i) | Bottoms (iii) |
|---|---|---|---|
| Boiling range °C. (atmospheric pressure) | 150–280 | 280–310 | >310 |
| wt % distilled | 13 | 72 | 15 |
| Composition % | | | |
| $C_8$-$C_{10}$ alcohols | 75 | | |
| $C_{16}$-$C_{20}$ ether | | 95 | |
| $C_{19}$-$C_{21}$ ether-alcohol | | 5 | |
| Acetals and heaviers | | | 65 |
| Characteristics | | | |
| Carbonyl number (mg KOH/g) | | 1.9 | |
| Acid number | | 0.8 | |

TABLE 6-continued

| | Alcohol (ii) | Composition (i) | Bottoms (iii) |
|---|---|---|---|
| Saponification number | | 4.3 | |
| Hydroxyl number | | 27 | |
| Specific gravity @ 20° C. | | 0.8211 | |
| Flash point (°C.) | | 138 | |
| Pour point (°C.) | | <−40 | |
| Viscosity (cs) 15° C. | | 11.5 | |
| 20° C. | | 9.5 | |
| 30° C. | | 6.7 | |
| 40° C. | | 5.1 | |

The products (i), (ia) and (ib) as produced in the preceding Examples and as generally corresponding to desired products of the method according to the invention have proved to be extremely useful materials in a variety of applications. In view of this utility the defined method is of particular merit since it enables industrially useful compositions and molecules to be produced on an industrial scale from feedstreams which are in fact the product streams of oxo alcohol plants. Hitherto such useful molecules have been available only as laboratory materials produced by specialised techniques not readily applicable to commercial situations.

The ether rich compositions (i) and (ia) have been found to be particularly useful as viscosity depressants for polyvinyl chloride (PVC) and for improving the low temperature flexibility of such materials as PVC, polyurethanes and silicone compositions. As may be seen from the preceding Examples the ethers are relatively high molecular weight compounds with low viscosities comparable to those of alcohols, and low volatilities because of their high molecular weights. This combination of low volatility, low viscosity and high molecular weight makes the compositions ideal for industrial solvent and diluent applications.

The ether-alcohol rich compositions (ib) are useful as precursors for the production of surfactants, for example by ethoxylation reactions. Thus they function as simple primary alcohols, but have high molecular weights. Moreover they are liquid at normal temperatures (as evidenced by their low pour point values) which make them easy to handle in all sorts of industrial applications.

I claim:

1. A method of producing an ether/ether-alcohol rich composition useful in solvent or surfactant precursor applications which consists essentially of:
   (a) subjecting the product of a $C_6$-$C_{12}$ olefin fraction hydroformylation reaction to hydrogenation; the hydroformylation being conducted at 120°–190° C. using a cobalt hydrocarbonyl catalyst in the presence of synthesis gas containing $H_2$ and CO and the hydrogenation being conducted at 120° C.–170° C. in the presence of a copper-chromium oxide or supported nickel hydrogenation catalyst;
   (b) distilling the hydrogenation product of (a) to obtain a mixture comprising 15–25 wt. % ether, 45–65 wt. % ether-alcohol, 5–25 wt. % acetal components, 2–10 wt. % ester components and 0–5 wt. % light alcohol components thereby separating said mixture from lighter ends;
   (b') subjecting said separated mixture of step (b) to catalytic steam cracking at a temperature of from 260°–380° C. using as a catalyst silica, alumina, mixed silica/alumina or titanium dioxide to form an ether enriched heavy product mixture and lighter materials;

(c) catalytically hydrogenating the heavy product mixture of step (b') at a temperature of 200°–250° C. and a pressure of 30–100 atmospheres to form an alcohol enriched product mixture using a copper-chromium oxide or supported nickel hydrogenation catalyst and, (d) subjecting the product mixture of step (c) to reflux distillation to separate (i) the desired ether/ether-alcohol rich composition containing at least 90 wt. % of ether/ether-alcohol from (ii) a lighter alcohol rich fraction and (iii) a heavier acetal rich fraction.

2. A method according to claim 1 wherein the ether/ether-alcohol rich composition (i) comprises at least 80 wt % ether.

3. A method according to claim 1 wherein the olefin employed in the olefin hydroformylation reaction is substantially C9 olefin and composition (i) comprises ethers of general formula $C_{10}H_{21}$—O—$C_{10}H_{21}$ which may be symmetrical or not.

4. A method according to claim 3 wherein composition (i) distils in the temperature range 310°–370° C. (adjusted to atmospheric pressure).

5. A method according to claim 1 wherein the composition (i) has at least one of carbonyl number (mgKOH/g) 0.5–2.5, acid number (mgKOH/g) less than 1.0, saponification number (mgKOH/g) 5–10 and hydroxyl number (mgKOH/g) less than 50.

6. A method according to claim 1 wherein the olefin employed in the olefin hydroformylation reaction is substantially C8 olefin and composition (i) comprises ethers of general formula $C_9H_{19}$—O—$C_9H_{19}$ which may be symmetrical or not.

7. A method according to claim 6 wherein composition (i) distils in the temperature range 285°–345° C. (adjusted to atmospheric pressure).

8. A method according to claim 1 wherein the heavy product mixture formed in step (b') comprises from 45–75 wt % ether component, from 20–35 wt % ether-alcohol component, from 1–6 wt % acetal component, from 0–10 wt % alcohol/aldehyde component and from 0–7 wt % ester component.

9. A method according to claim 1 wherein the heavy product mixture formed in step (b') has at least one of the characterising features selected from a specific gravity of from 0.81–0.87, distillation characteristics at atmospheric pressure of initial boiling point from 240°–310° C. and final boiling point of from 310°–380° C., a flash point of from 140°–170° C., a pour point of less than −30° C., a carbonyl number (mg KOH/g) of from 20–30, an acidity (mg KOH/g) of from 2–7, a saponification number (mg KOH/g) of from 10–20 and an hydroxyl number (mg KOH/g) of from 30–50.

10. A method according to claim 1 wherein the product mixture of step (c) has at least one of the characterising features selected from a specific gravity of from 0.81–0.87, distillation characteristics at atmospheric pressure of initial boiling point from 240°–310° C. and final boiling point of from 310°–380° C., a flashpoint of from 140°–170° C., a pour point of less than −30° C., a carbonyl number (mg KOH/g) of from 0.5–3.0, an acidity (mg KOH/g) of from 0.5–2.0, a saponification number (mg KOH/g) of from 5–10 and an hydroxyl number (mg KOH/g) of from 70–90.

11. A method according to claim 1 wherein the product mixture of step (c) comprises from 45–75 wt % ether component, from 10–35 wt % ether-alcohol component, from 1–6 wt % acetal component, from 0–15 wt % alcohol/aldehyde component and from 0–7 wt % ester component.

12. A method according to claim 1 wherein the catalyst of stage (b') is alumina.

13. A method according to claim 1 wherein stage (b') is performed using steam and said mixture at a weight ratio in the range 0.1:1–2:1 and at a total pressure of from 1–10 atm. abs.

* * * * *